United States Patent
So et al.

(10) Patent No.: US 10,513,718 B2
(45) Date of Patent: Dec. 24, 2019

(54) METHOD OF PRODUCING POLYUNSATURATED FATTY ACID

(71) Applicant: City University of Hong Kong, Kowloon (HK)

(72) Inventors: Lok Man So, New Territories (HK);
Man Chak Tse, New Territories (HK);
Kai Kin Chi, New Territories (HK);
Yuen Chong Kong, Kowloon (HK);
Sin Yu Yeung, New Territories (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 15/614,896

(22) Filed: Jun. 6, 2017

(65) Prior Publication Data
US 2018/0346944 A1    Dec. 6, 2018

(51) Int. Cl.
| | |
|---|---|
| *C12P 7/64* | (2006.01) |
| *C12N 9/10* | (2006.01) |
| *C12N 9/02* | (2006.01) |
| *C12N 9/00* | (2006.01) |

(52) U.S. Cl.
CPC .......... *C12P 7/6427* (2013.01); *C12N 9/0071* (2013.01); *C12N 9/10* (2013.01); *C12N 9/93* (2013.01); *C12Y 114/19* (2013.01); *C12Y 114/19004* (2013.01); *C12Y 602/01003* (2013.01)

(58) Field of Classification Search
USPC .............................. 435/252.3, 134; 800/281
See application file for complete search history.

(56) References Cited

U.S. PATENT DOCUMENTS

| | | | |
|---|---|---|---|
| 5,658,767 A | 8/1997 | Kyle | |
| 7,645,604 B2 * | 1/2010 | Damude | ................. C11B 1/025 435/134 |
| 7,678,560 B2 * | 3/2010 | Damude | .............. C12N 9/0083 435/254.11 |
| 8,273,958 B2 * | 9/2012 | Napier | ................. C12N 9/0083 800/298 |
| 2006/0051847 A1 | 3/2006 | Gunnarsson et al. | |
| 2006/0168687 A1 | 7/2006 | Renz et al. | |
| 2008/0155705 A1 | 6/2008 | Zank et al. | |

* cited by examiner

*Primary Examiner* — Tekchand Saidha
(74) *Attorney, Agent, or Firm* — Renner Kenner Greive Bobak Taylor & Weber

(57) ABSTRACT

A method of producing a polyunsaturated fatty acid in a transgenic bacterium, includes: introducing a recombinant plasmid into a bacteria cell to obtain the transgenic bacterium, wherein the recombinant plasmid comprises a polynucleotide encoding one or more elongase and one or more desaturase; incubating the transgenic bacterium in a medium containing a fatty acid substrate; harvesting the transgenic bacterium, and extracting the polyunsaturated fatty acid from the transgenic bacterium. A method of converting linoleic acid to arachidonic acid and a cassette and recombinant plasmid comprising nucleic acid sequences for the above methods are also provided.

11 Claims, 2 Drawing Sheets

Specification includes a Sequence Listing.

SEQUENCE LISTING

```
<160> NUMBER OF SEQ ID NOS: 4

<210> SEQ ID NO 1
<211> LENGTH: 780
<212> TYPE: DNA
<213> ORGANISM: Artificial Sequence
<220> FEATURE:
<223> OTHER INFORMATION: Synthesized

<400> SEQUENCE: 1
atggaagtgg tgaatgaaat tgtgagcatt ggtcaagaag ttctgccgaa agttgattat      60
gcccagctgt ggtcagatgc aagccattgt gaagttctgt atctgagcat tgcctttgtg     120
atcctgaaat taccctggg tccgctgggt cctaaaggtc agagccgtat gaaatttgtg     180
ttcaccaatt ataacctgct gatgagcatt tatagcctgg gtagctttct gagcatggca     240
tatgcaatgt ataccattgg tgtgatgagc gataattgcg aaaaagcctt tgataacaac     300
gtgtttcgta ttaccaccca gctgtttat  ctgtccaaat tcctggaata tatcgatagc     360
ttttatctgc cgctgatggg taaaccgctg acctggctgc aatttttca  tcatctgggt     420 gcaccgatgg atatgtggct gttttacaat tatcgtaatg aagccgtgtg gatctttgtt     480
ctgctgaatg gttttatcca ctggatcatg tatggctatt attggacccg tctgatcaaa     540 ctgaaattc cgatgccgaa aagcctgatt accagcatgc agattattca gtttaacgtg     600
ggcttttata tcgtgtggaa atatcgtaac attccgtgct atcgtcagga tggtatgcgt     660
atgtttggct ggttttcaa ctatttctat gttggcaccg ttctgtgtct gtttctgaac     720
ttttatgtgc agacctatat cgtgcgcaaa cacaaggtg  ccaaaaaaat ccagtaataa     780

<210> SEQ ID NO 2
<211> LENGTH: 1272
<212> TYPE: DNA
<213> ORGANISM: Artificial Sequence
<220> FEATURE:
<223> OTHER INFORMATION: Synthesized

<400> SEQUENCE: 2
atggttaaat ccaaacgtca ggcactcccc ctgactatcg acggtaccac ctacgatgtt      60
agtgcgtggg ttaactttca tcccggtggt gcggaaatta tcgagaacta tcagggtcgt     120
gatgccacag atgcatttat ggtcatgcac agccaggaag cctttgataa gttaaaacgt     180
atgccaaaaa ttaacccgag ctccgagtta ccgccgcagg ccgcagtcaa cgaggctcaa     240 gaggacttc  gtaaactgcg cgaagaactt atcgctacgg gtatgttga  cgctagcccg     300
```

| | |
|---|---|
| ctgtggtaca gttataaaat ttctaccacg ctgggcctgg gtgtgctggg ctattttctc | 360 |
| atggtacaat accaaatgta tttcattggt gcggttctgc tgggcatgca ctatcaacag | 420 |
| atgggttggc tgagccatga catctgccat catcaaacgt tcaaaaaccg caattggaac | 480 |
| aaccttgtgg gattagtgtt tggtaacggt ttgcagggtt tctcggtcac gtggtggaaa | 540 |
| gatcggcata atgcgcatca ctctgccact aacgtccagg gtcatgaccc ggacattgat | 600 |
| aatttaccgc ttctggcctg gagcgaggat gatgtgacac gcgcgagccc gattagccgc | 660 |
| aaactgatcc aattccagca gtattacttc ttagttattt gcatcttgct gcggttcatt | 720 |
| tggtgttttc agtcggtgtt aaccgtccgc tctctgaaag accgcgataa tcagttctac | 780 |
| cgcagccagt ataaaaaaga agcaatcggt ctggcgctgc attggactct gaaaactctg | 840 |
| tttcatttat tcttcatgcc tagcattctg acgtctcttc tcgtcttctt cgttagcgag | 900 |
| ctggtcgggg gttttgggat tgctattgta gttttcatga accattatcc tcttgaaaaa | 960 |
| attggagact cagtctggga tgggcatgga ttttcagtag gtcaaattca cgaaaccatg | 1020 |
| aatatccgtc gtggtattat cacgagttgg ttctttgggg ggcttaacta ccagattgaa | 1080 |
| catcacctgt ggccgacgtt gccgcgtcac aacctgaccg cggttagcta tcaggttgag | 1140 |
| cagctgtgcc agaaacataa tctgccgtat cgcaacccgc tgccgcatga agggttggta | 1200 |
| attctcctgc gttacttagc agtattcgcg cgcatggcag aaaaacaacc ggcgggtaaa | 1260 |
| gctttgtaat aa | 1272 |

<210> SEQ ID NO 3
<211> LENGTH: 1353
<212> TYPE: DNA
<213> ORGANISM: Artificial Sequence
<220> FEATURE:
<223> OTHER INFORMATION: Synthesized

<400> SEQUENCE: 3

| | |
|---|---|
| atggcactga gcctgaccac cgaacagctg ctggaacgtc cggatctggt tgcaattgat | 60 |
| ggtattctgt atgatctgga aggtctggca aaagttcatc cgggtggtga tctgattctg | 120 |
| gcaagcggtg caagtgatgc aagtccgctg ttttatagca tgcatccgta tgttaaaccg | 180 |
| gaaaatagca aactgctgca acagttcgtt cgtggtaaac atgatcgtac cagcaaagat | 240 |
| atcgtgtata cctatgatag cccgtttgca caggatgtta aacgtaccat gcgtgaagtt | 300 |
| atgaaaggtc gtaattggta tgcaacaccg ggtttttggc tgcgtaccgt tggtattatt | 360 |
| gcagttaccg cattttgtga atggcattgg gcaaccaccg gtatggttct gtggggtctg | 420 |
| ctgaccggtt ttatgcacat gcagattggt ctgagcattc agcatgatgc aagccatggt | 480 |
| gcaattagca aaaaaccgtg ggttaatgca ctgtttgcct atggtattga tgttattggt | 540 |
| agcagccgtt ggatttggct gcaaagccat attatgcgtc atcataccta tccaatcag | 600 |
| catggtctgg atctggatgc agaaagcgca gaaccgtttc tggtttttca taattatccg | 660 |
| gcagcaaata ccgcacgcaa atggtttcat cgttttcagg catggtatat gtatctggtt | 720 |
| ctgggtgcat atggtgttag cctggtttat aatccgctgt atatctttcg catgcagcat | 780 |
| aatgatacca ttccggaaag cgttaccgca atgcgtgaaa atggttttct cgtcgttat | 840 |
| cgtaccctgg catttgttat gcgtgccttt tttatctttc gtaccgcctt tctgccgtgg | 900 |
| tatctgaccg gcaccagcct gctgattaca attccgctgg ttccgaccgc aaccggtgca | 960 |
| tttctgacct tttttttcat tctgagccac aactttgatg cagcgaacg tattccggat | 1020 |
| aaaaactgta aagtgaaaag cagcgagaaa gatgttgaag ccgatcagat cgattggtat | 1080 |

```
cgtgcacagg ttgaaaccag cagcacctat ggtggtccga ttgcaatgtt ttttaccggt    1140
ggcctgaatt ttcagattga acatcacctg tttccgcgta tgagcagctg gcattatccg    1200
tttgttcagc aggcagttcg tgaatgttgt gaacgtcatg gtgttcgcta tgtgttttat    1260
ccgaccattg tgggtaacat tattagcacc ctgaaatata tgcataaagt gggtgttgtg    1320
cactgcgtta aagatgccca ggatagctaa taa                                 1353
```

<210> SEQ ID NO 4
<211> LENGTH: 8947
<212> TYPE: DNA
<213> ORGANISM: Artificial Sequence
<220> FEATURE:
<223> OTHER INFORMATION: Synthesized

<400> SEQUENCE: 4

```
aactacgtca ggtggcactt tcggggaaa tgtgcgcgga acccctattt gtttattttt     60
ctaaatacat tcaaatatgt atccgctcat gagacaataa ccctgataaa tgcttcaata    120
atattgaaaa aggaagagta tgagtattca acatttccgt gtcgccctta ttccctttt    180 tgcggcattt tgccttcctg tttttgctca cccagaaacg ctggtgaaag taaaagatgc    240
tgaagatcag ttgggtgcac gagtgggtta catcgaactg gatctcaaca gcggtaagat    300
ccttgagagt tttcgccccg aagaacgttt cccaatgatg agcacttta aagttctgct    360 atgtggcgcg gtattatccc gtgttgacgc cgggcaagag caactcggtc gccgcataca    420
ctattctcag aatgacttgg ttgagtactc accagtcaca gaaaagcatc ttacggatgg    480
catgacagta agagaattat gcagtgctgc cataaccatg agtgataaca ctgcggccaa    540
cttacttctg acaacgatcg gaggaccgaa ggagctaacc gcttttttgc acaacatggg    600
ggatcatgta actcgccttg atcgttggga accggagctg aatgaagcca taccaaacga    660
cgagcgtgac accacgatgc ctgtagcaat ggcaacaacg ttgcgcaaac tattaactgg    720
cgaactactt actctagctt cccggcaaca attaatagac tggatggagg cggataaagt    780
tgcaggacca cttctgcgct cggcccttcc ggctggctgg tttattgctg ataaatctgg    840
agccggtgag cgtgggtctc gcggtatcat tgcagcactg gggccagatg gtaagccctc    900
ccgtatcgta gttatctaca cgacggggag tcaggcaact atggatgaac gaaatagaca    960
gatcgctgag ataggtgcct cactgattaa gcattggtaa ctgtcagacc aagtttactc    1020
atatatactt tagattgatt taccccggtt gataatcaga aaagccccaa aacaggaag    1080 attgtataag caaatattta aattgtaaac gttaatattt tgttaaaatt cgcgttaaat    1140
ttttgttaaa tcagctcatt ttttaaccaa taggccgaaa tcggcaaaat cccttataaa    1200
tcaaaagaat agcccgagat agggttgagt gttgttccag tttggaacaa gagtccacta    1260
ttaaagaacg tggactccaa cgtcaaaggg cgaaaaaccg tctatcaggg cgatggccca    1320
ctacgtgaac catcacccaa atcaagtttt tggggtcga ggtgccgtaa agcactaaat    1380
cggaacccta aagggagccc ccgatttaga gcttgacggg gaaagccggc gaacgtggcg    1440
agaaaggaag ggaagaaagc gaaaggagcg ggcgctaggg cgctggcaag tgtagcggtc    1500
acgctgcgcg taaccaccac acccgccgcg cttaatgcgc cgctacaggg cgcgtaaaag    1560
gatctaggtg aagatccttt ttgataatct catgaccaaa atcccttaac gtgagttttc    1620
gttccactga gcgtcagacc ccgtagaaaa gatcaaagga tcttcttgag atcctttttt    1680
tctgcgcgta atctgctgct tgcaaacaaa aaaaccaccg ctaccagcgg tggtttgttt    1740
```

-continued

```
gccggatcaa gagctaccaa ctcttttcc gaaggtaact ggcttcagca gagcgcagat    1800
accaaatact gtccttctag tgtagccgta gttaggccac cacttcaaga actctgtagc    1860
accgcctaca tacctcgctc tgctaatcct gttaccagtg gctgctgcca gtggcgataa    1920
gtcgtgtctt accgggttgg actcaagacg atagttaccg gataaggcgc agcggtcggg    1980
ctgaacgggg ggttcgtgca cacagcccag cttggagcga acgacctaca ccgaactgag    2040
atacctacag cgtgagctat gagaaagcgc cacgcttccc gaagggagaa aggcggacag    2100
gtatccggta agcggcaggg tcggaacagg agagcgcacg agggagcttc caggggggaaa   2160 cgcctggtat ctttatagtc ctgtcgggtt tcgccacctc tgacttgagc gtcgattttt    2220
gtgatgctcg tcagggggggc ggagcctatg aaaaacgcc agcaacgcgg ccttttttacg    2280 gttcctggcc ttttgctggc cttttgctca catgttcttt cctgcgttat ccctgattc     2340 tgtggataac cgtattaccg ccttttgagtg agctgatacc gctcgccgca gccgaacgac    2400
cgagcgcagc gagtcagtga gcgaggaagc tatggtgcac tctcagtaca atctgctctg    2460
atgccgcata gttaagccag tatacactcc gctatcgcta cgtgactggg tcatggctgc    2520
gccccgacac ccgccaacac ccgctgacgc gccctgacgg gcttgtctgc tcccggcatc    2580
cgcttacaga caagctgtga ccgtctccgg gagctgcatg tgtcagaggt tttcaccgtc    2640
atcaccgaaa cgcgcgaggc agctgcggta aagctcatca gcgtggtcgt gcagcgattc    2700
acagatgtct gcctgttcat ccgcgtccag ctcgttgagt ttctccagaa gcgttaatgt    2760
ctggcttctg ataaagcggg ccatgttaag ggcggttttt tcctgtttgg tcactgatgc    2820
ctccgtgtaa gggggatttc tgttcatggg ggtaatgata ccgatgaaac gagagaggat    2880
gctcacgata cgggttactg atgatgaaca tgcccggtta ctggaacgtt gtgagggtaa    2940
acaactggcg gtatggatgc ggcgggacca gagaaaaatc actcagggtc aatgccagcc    3000
gaacgccagc aagacgtagc ccagcgcgtc ggccgccatg ccggcgataa tggcctgctt    3060
ctcgccgaaa cgtttggtgg cgggaccagt gacgaaggct tgagcgaggg cgtgcaagat    3120
tccgaatacc gcaagcgaca ggccgatcat cgtcgcgctc cagcgaaagc ggtcctcgcc    3180
gaaaatgacc cagagcgctg ccggcacctg tcctacgagt tgcatgataa agaagacagt    3240
cataagtgcg gcgacgatag tcatgccccg cgcccaccgg aaggagctga ctgggttgaa    3300
ggctctcaag gcatcggtc gagatcccgg tgcctaatga gtgagctaac ttacattaat    3360
tgcgttgcgc tcactgcccg ctttccagtc gggaaacctg tcgtgccagc tgcattaatg    3420
aatcggccaa cgcgcgggga gaggcggttt gcgtattggg cgccagggtg ttttttcttt    3480
tcaccagtga cgggcaac agctgattgc ccttcaccgc ctggccctga gagagttgca     3540
gcaagcggtc cacgctggtt tgccccagca ggcgaaaatc ctgtttgatg gtggttaacg    3600
gcgggatata acatgagctg tcttcggtat cgtcgtatcc cactaccgag atgtccgcac    3660
caacgcgcag cccggactcg gtaatggcgc gcattgcgcc cagcgccatc tgatcgttgg    3720
caaccagcat cgcagtggga acgatgccct cattcagcat ttgcatggtt tgttgaaaac    3780
cggacatggc actccagtcg ccttcccgtt ccgctatcgg ctgaatttga ttgcgagtga    3840
gatatttatg ccagccagcc agacgcagac gcgccgagac agaacttaat gggcccgcta    3900
acagcgcgat ttgctggtga cccaatgcga ccagatgctc cacgcccagt cgcgtaccgt    3960
cttcatggga gaaaataata ctgttgatgg gtgtctggtc agagacatca agaaataacg    4020
ccggaacatt agtgcaggca gcttccacag caatggcatc ctggtcatcc agcggatagt    4080
taatgatcag cccactgacg cgttgcgcga agattgtgc caccgccgct ttacaggctt    4140
```

```
cgacgccgct tcgttctacc atcgacacca ccacgctggc acccagttga tcggcgcgag    4200
atttaatcgc cgcgacaatt tgcgacggcg cgtgcagggc cagactggag gtggcaacgc    4260
caatcagcaa cgactgtttg cccgccagtt gttgtgccac gcggttggga atgtaattca    4320
gctccgccat cgccgcttcc acttttcccc gcgttttcgc agaaacgtgg ctggcctggt    4380
tcaccacgcg ggaaacggtc tgataagaga caccggcata ctctgcgaca tcgtataacg    4440
ttactggttt cacattcacc accctgaatt gactctcttc cgggcgctat catgccatac    4500
cgcgaaaggt tttgcgccat cgatggtgt ccgggatctc gacgctctcc cttatgcgac    4560
tcctgcatta ggaagcagcc cagtagtagg ttgaggccgt tgagcaccgc cgccgcaagg    4620
aatggtgcat gccggcatgc cgccctttcg tcttcaagaa ttaattccca attccccagg    4680
catcaaataa aacgaaaggc tcagtcgaaa gactgggcct ttcgttttat ctgttgtttg    4740
tcggtgaacg ctctcctgag taggacaaat ccgccgggag cggatttgaa cgttgcgaag    4800
caacggcccg gagggtggcg gcaggacgcc cgccataaa ctgccaggaa ttaattcccc    4860
aggcatcaaa taaaacgaaa ggctcagtcg aaagactggg cctttcgttt tatctgttgt    4920
ttgtcggtga acgctctcct gagtaggaca atccgccgg gagcggattt gaacgttgcg    4980
aagcaacggc ccggagggtg gcgggcagga cgcccgccat aaactgccag gaattaattc    5040
cccaggcatc aaataaaacg aaaggctcag tcgaaagact gggccttcg ttttatctgt    5100 tgtttgtcgg tgaacgctct cctgagtagg acaaatccgc cgggagcgga tttgaacgtt    5160
gcgaagcaac ggcccggagg gtggcgggca ggacgcccgc cataaactgc caggaattaa    5220
ttccccaggc atcaaataaa acgaaaggct cagtcgaaag actgggcctt tcgttttatc    5280
tgttgtttgt cggtgaacgc tctcctgagt aggacaaatc cgcgggagc ggatttgaac    5340 gttgcgaagc aacggcccgg agggtggcgg gcaggacgcc cgccataaac tgccaggaat    5400
taattcccca ggcatcaaat aaaacgaaag gctcagtcga aagactgggc ctttcgtttt    5460
atctgttgtt tgtcggtgaa cgctctcctg agtaggacaa atccgccggg agcggatttg    5520
aacgttgcga gcaacggcc cggagggtgg cgggcaggac gcccgccata aactgccagg    5580
aattggggat cggaattaat tcccggttta accggggat ctcgatcccg cgaaattaat    5640
acgactcact atagggggaat tgtgagcgga taacaattcc cctctagaaa taattttgtt    5700
taactttaag aaggagatat acatatggtc atgagccaga aaaccctgtt tacaaagtct    5760
gctctcgcag tcgcagtggc acttatctcc acccaggcct ggtcggcagg cttcagtta    5820 aacgaatttt cttcctctgg cctgggccgg gcttattcag gggaaggcgc aattgccgat    5880
gatgcaggta acgtcagccg taaccccgca ttgattacta tgtttgaccg cccgacattt    5940
tctgcgggtg cggtttatat tgacccggat gtaaatatca gcggaacgtc tccatctggt    6000
cgtagcctga agccgataaa catcgcgcct acggcatggg ttccgaacat gcactttgtt    6060
gcaccgatta cgaccaattt ggttggggc gcttctatta cctctaacta tggtctggct    6120
acagagttta acgatactta tgcaggcggc tctgtcgggg gtacaaccga ccttgaaacc    6180
atgaacctga acttaagcgg tgcgtatcgc ttaaataatg catggagctt tggtcttggt    6240
ttcaacgccg tctacgctcg cgcgaaaatt gaacgtttcg caggcgatct ggggcagttg    6300
gttgctggcc aaattatgca atctcctgct ggccaaactc agcaagggca agcattggca    6360
gctaccgcca acggtattga cagtaatacc aaaatcgctc atctgaacgg taaccagtgg    6420
ggctttggct ggaacgccgg aatcctgtat gaactggata aaaataaccg ctatgcactg    6480
```

```
acctaccgtt ctgaagtgaa aattgacttc aaaggtaact acagcagcga tcttaatcgt    6540
gcgtttaata actacggttt gccaattcct accgcgacag gtggcgcaac gcaatcgggt    6600
tatctgacgc tgaacctgcc tgaaatgtgg gaagtgtcag gttataaccg tgttgatcca    6660
cagtgggcga ttcactatag cctggcttac accagctgga gtcagttcca gcagctgaaa    6720
gcgacctcaa ccagtggcga cacgctgttc cagaaacatg aaggctttaa agatgcttac    6780
cgcatcgcgt tgggtaccac ttattactac gatgataact ggaccttccg taccggtatc    6840
gcctttgatg acagcccagt tcctgcacag aatcgttcta tctccattcc ggaccaggac    6900
cgtttctggc tgagtgcagg tacgacttac gcatttaata aagatgcttc agtcgacgtt    6960
ggtgtttctt atatgcacgg tcagagcgtg aaaattaacg aaggcccata ccagttcgag    7020
tctgaaggta aagcctggct gttcggtact aactttaact acgcgttctg atgaggatcc    7080
aggaggacag ctatgaagaa ggtttggctt aaccgttatc ccgcggacgt tccgacggag    7140
atcaaccctg accgttatca atctctggta gatatgtttg agcagtcggt cgcgcgctac    7200
gccgatcaac ctgcgtttgt gaatatgggg gaggtaatga ccttccgcaa gctggaagaa    7260
cgcagtcgcg cgtttgccgc ttatttgcaa caagggttgg ggctgaagaa aggcgatcgc    7320
gttgcgttga tgatgcctaa tttattgcaa tatccggtgg cgctgtttgg cattttgcgt    7380
gccgggatga tcgtcgtaaa cgttaacccg ttgtataccc cgcgtgagct gagcatcag    7440
cttaacgata gcggcgcatc ggcgattgtt atcgtgtcta actttgctca cactggaa    7500
aaagtggttg ataaaaccgc cgttcagcac gtaattctga cccgtatggg cgatcagcta    7560
tctacggcaa aaggcacggt agtcaatttc gttgttaaat acatcaagcg tttggtgccg    7620
aaataccatc tgccagatgc catttcattt cgtagcgcac tgcataacgg ctaccggatg    7680
cagtacgtca aacccgaact ggtgccggaa gatttagctt ttctgcaata caccggcggc    7740
accactggtg tggcgaaagg cgcgatgctg actcaccgca atatgctggc gaacctggaa    7800
caggttaacg cgacctatgg tccgctgttg catccgggca aagagctggt ggtgacggcg    7860
ctgccgctgt atcacatttt tgccctgacc attaactgcc tgctgtttat cgaactgggt    7920
gggcagaacc tgcttatcac taacccgcgc gatattccag ggttggtaaa agagttagcg    7980
aaatatccgt ttaccgctat cacgggcgtt aacaccttgt tcaatgcgtt gctgaacaat    8040
aaagagttcc agcagctgga tttctccagt ctgcatcttt ccgcaggcgg tgggatgcca    8100
gtgcagcaag tggtggcaga cgttgggtg aaactgaccg gacagtatct gctggaaggc    8160
tatgccctta ccgagtgtgc gccgctggtc agcgttaacc catatgatat tgattatcat    8220
agtggtagca tcggtttgcc ggtgccgtcg acggaagcca aactggtgga tgatgatgat    8280
aatgaagtac caccaggtca accgggtgag ctttgtgtca aaggaccgca ggtgatgctg    8340
ggttactggc agcgtcccga tgctaccgat gaaatcatca aaaatggctg gttacacacc    8400
ggcgacatcg cggtaatgga tgaagaagga ttcctgcgca ttgtcgatcg taaaaaagac    8460
atgattctgg tttccggttt taacgtctat cccaacgaga ttgaagatgt cgtcatgcag    8520
catcctggcg tacaggaagt cgcggctgtt ggcgtacctt ccggctccag tggtgaagcg    8580
gtgaaaatct tcgtagtgaa aaaagatcca tcgcttaccg aagagtcact ggtgactttt    8640
tgccgccgtc agctcacggg atacaaagta ccgaagctgg tggagtttcg tgatgagtta    8700
ccgaaatcta acgtcggaaa aattttgcga cgagaattac gtgacgaagc gcgcggcaaa    8760
gtggacaata aagcctgaac tagtctcgag gttaattaag cggccgcatt gatccggctg    8820
ctaacaaagc ccgaaaggaa gctgagttgg ctgctgccac cgctgagcaa taactagcat    8880
```

```
aaccccttgg ggcctctaaa cgggtcttga ggggtttttt gctgaaagga ggaactatat    8940
ccggatt                                                              8947
```

METHOD OF PRODUCING POLYUNSATURATED FATTY ACID

SEQUENCE LISTING

The Sequence Listing file entitled "sequencelisting" having a size of 16,856 bytes and a creation date of 6 Jun. 2017 that was filed with the patent application is incorporated herein by reference in its entirety.

TECHNICAL FIELD

This invention relates to a method of producing a polyunsaturated fatty acid, in particular but not exclusively, a method of producing a polyunsaturated fatty acid in a transgenic microorganism. This invention also relates to a recombinant plasmid comprising a polypeptide for encoding one or more enzymes for the above method.

BACKGROUND OF THE INVENTION

Arachidonic acid (ARA) is a polyunsaturated fatty acid belonging to the class of omega-6 fatty acid. Arachidonic acid can be found in animal and human, and is prevalent in brain, muscles, liver and blood tissues. It is also an essential fatty acid which cannot be synthesized in humans but necessary for growth and development. Nowadays, arachidonic acid is generally applied to an infant formula to provide sufficient nutrients to babies.

Methods have been developed to produce arachidonic acid in eukaryotic cells. For example, transgenic techniques have been applied to transform a fungus so as to obtain a fungal oil containing arachidonic acid. Currently, the main source of arachidonic acid is obtained from the transgenic *Mortierella* sp. However, the production cost of such a fungal oil is relatively high and the growth rate of the fungus is slow, e.g. at a rate of 48 hours per doubling.

Accordingly, there remains a strong need for developing an effective method or at least an alternative method to produce arachidonic acid, especially with a lower cost with good yield.

SUMMARY OF THE INVENTION

In the first aspect, the present invention provides a method of producing a polyunsaturated fatty acid in a transgenic bacterium, comprising steps of:
  (a) introducing a recombinant plasmid into a bacterium to obtain the transgenic bacterium, wherein the recombinant plasmid comprises a polynucleotide encoding one or more elongase and one or more desaturase;
  (b) incubating the transgenic bacterium in a medium containing a fatty acid substrate;
  (c) harvesting the transgenic bacterium, and extracting the polyunsaturated fatty acid from the transgenic bacterium.

In an embodiment, the bacterium belongs to the genus selected from the group consisting of *Bifidobacterium, Lactobacillus* and *Escherichia*. In particular, the bacterium is *E. coli*.

Preferably, the polyunsaturated fatty acid comprises a hydrocarbon backbone composed of 20 to 24 carbon atoms with four or more carbon-carbon double bonds; and the fatty acid substrate is a polyunsaturated fatty acid and comprises a hydrocarbon backbone composed of 16 to 18 carbon atoms with one or more carbon-carbon double bond. In particular, the fatty acid substrate is linoleic acid.

The polyunsaturated fatty acid is preferably an omega-3 fatty acid, an omega-6 fatty acid or an omega-9 fatty acid. In a particular embodiment, the polyunsaturated fatty acid is arachidonic acid, eicosapentaenoic acid, or docosahexaenoic acid.

In an embodiment, the polynucleotide encodes an elongase and two desaturases. In particular, the polynucleotide comprises a first nucleic acid sequence provided in SEQ ID NO: 1, a second nucleic acid sequence provided in SEQ ID NO: 2 and a third nucleic acid sequence provided in SEQ ID NO. 3.

In an embodiment, the recombinant plasmid comprises a promoter, a sequence encoding a long-chain fatty acid transport protein precursor, and a sequence encoding a long chain fatty acryl-CoA ligase.

In a second aspect, the present invention provides a method of converting linoleic acid to arachidonic acid in particular in a transgenic bacterium, comprising steps of:
  (i) preparing a transgenic bacterium by introducing a recombinant plasmid into a bacterium, wherein the recombinant plasmid comprises a polynucleotide encoding one or more elongase and one or more desaturase;
  (ii) incubating the transgenic bacterium in a medium containing linoleic acid; and
  (iii) harvesting the transgenic bacterium and extracting arachidonic acid from the transgenic bacterium.

In a third aspect, the present invention provides a cassette comprising a first nucleic acid sequence provided in SEQ ID NO: 1, a second nucleic acid sequence provided in SEQ ID NO: 2 and a third nucleic acid sequence provided in SEQ ID NO. 3 as described above.

Furthermore, the present invention pertains to a recombinant plasmid comprising a first nucleic acid sequence provided in SEQ ID NO: 1, a second nucleic acid sequence provided in SEQ ID NO: 2, a third nucleic acid sequence provided in SEQ ID NO. 3, a promoter sequence, a sequence encoding a long-chain fatty acid transport protein precursor, and a sequence encoding a long chain fatty acryl-CoA ligase.

Still further, the present invention also pertains to a transgenic bacterium comprising said recombinant plasmid. In an embodiment, the bacterium belongs to the genus selected from the group consisting of *Bifidobacterium, Lactobacillus* and *Escherichia*. In particular, the bacterium is *E. coli*.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

DETAILED DESCRIPTION OF THE EMBODIMENTS

Figure 1:
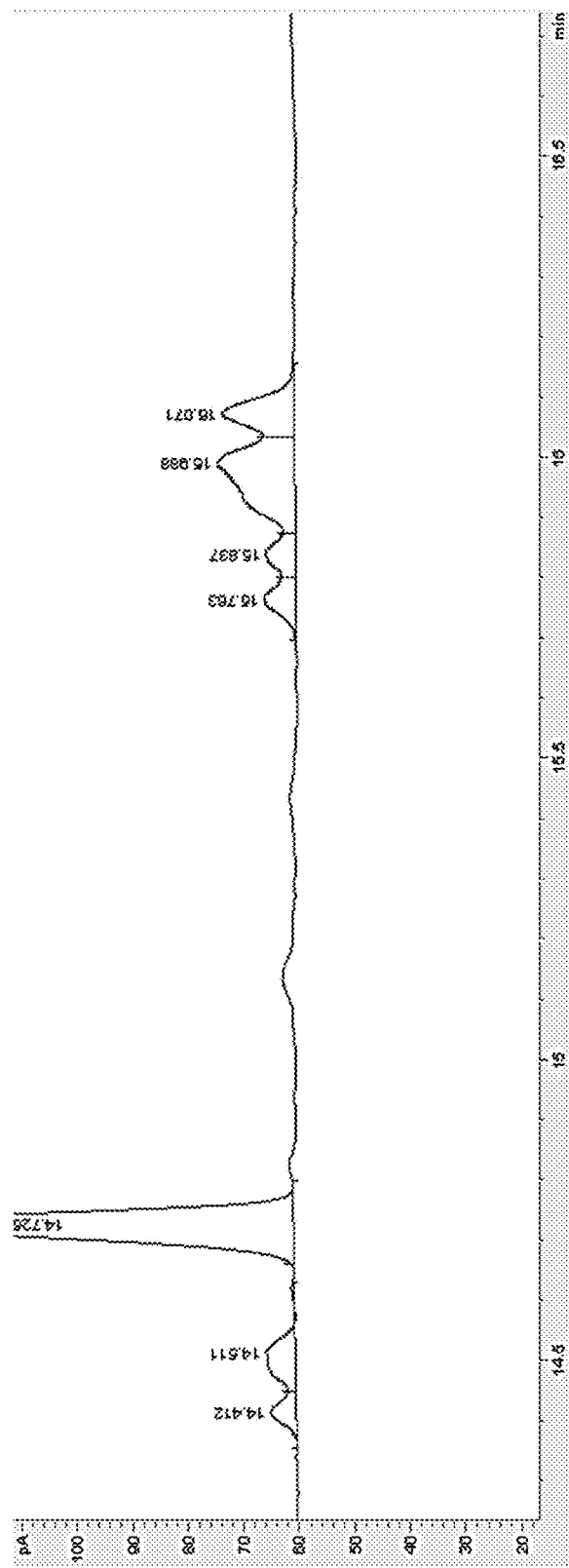
FIG. 1 is a gas chromatogram profile of fatty acids extracted from the wild type *E. coli*.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention in the first aspect provides a method of producing a polyunsaturated fatty acid in a transgenic microorganism, preferably a transgenic bacterium, comprising steps of:
(a) introducing a recombinant plasmid into a bacterium to obtain the transgenic bacterium, wherein the recombinant plasmid comprises a polynucleotide encoding one or more elongase and one or more desaturase;
(b) incubating the transgenic bacterium in a medium containing a fatty acid substrate
(c) harvesting the transgenic bacterium, and extracting the polyunsaturated fatty acid from the transgenic bacterium.

The term "polyunsaturated fatty acid" as used herein refers to a long hydrocarbon chain having a terminal carboxylic group and a long hydrocarbon backbone composed of 16 or more carbon atoms with more than one carbon-carbon double bond. The skilled person in the art would appreciate that polyunsaturated fatty acid may be an omega fatty acid, or a conjugated fatty acid.

The term "omega fatty acids" relates to a family of polyunsaturated unsaturated fatty acids having two or more carbon-carbon double bonds separated by a methylene unit ($-CH_2-$) and it includes omega-3 fatty acids, omega-6 fatty acids and omega-9 fatty acids. Omega-3 fatty acid has a carbon-carbon double bond at the third carbon atom from the hydrocarbon end, omega-6 fatty acid has a carbon-carbon double bond at the sixth carbon atom from the hydrocarbon end and omega-9 fatty acid has a carbon-carbon double bond at the ninth carbon atom from the hydrocarbon end. Table 1 lists out some omega fatty acids which may be applied in this present invention.

TABLE 1

Omega fatty acids

| Common name | Lipid name | Chemical name |
| --- | --- | --- |
| Roughanic acid | 16:3 (n-3) | all-cis-7,10,13-hexadecatrienoic acid |
| α-linolenic acid (ALA) | 18:3 (n-3) | all-cis-9,12,15-octadecatrienoic acid |
| Stearidonic acid (SDA) | 18:4 (n-3) | all-cis-6,9,12,15,-octadecatetraenoic acid |
| Linoleic acid | 18:2 (n-6) | all-cis-9,12-octadecadienoic acid |
| γ-linolenic acid (GLA) | 18:3 (n-6) | all-cis-6,9,12-octadecatrienoic acid |
| Oleic acid | 18:1 (n-9) | cis-9-octadecenoic acid |
| Eicosatrienoic acid (ETE) | 20:3 (n-3) | all-cis-11,14,17-eicosatrienoic acid |
| Eicosatertraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Eicosadienoic acid | 20:2 (n-6) | all-cis-11,14-eicosadienoic acid |
| Dihomo-γ-linolenic acid (DGLA) | 20:3 (n-6) | all-cis-8,11,14-eicosatrienoic acid |
| Arachidonic acid (ARA) | 20:4 (n-6) | all-cis-5,8,11,14-eicosatetraenoic acid |
| Eicosenoic acid | 20:1 (n-9) | cis-11-eicosenoic acid |
| Gondoic acid | 20:1 (n-9) | cis-11-lcosenoic acid |
| Mead acid | 20:3 (n-9) | all-cis-5,8,11-eicosatrienoic acid |
| Docosapentaenoic acid (DPA) | 22:5 (n-3) | all-cis-7,10,13,16,19-docosapentaenoic acid |
| Docosahexaenoic acid (DHA) | 22:6 (n-3) | all-cis-4,7,10,13,16,19-docosahexaenoic acid |
| Docosadienoic acid | 22:2 (n-6) | all-cis-13,16-docosadienoic acid |
| Adrenic acid | 22:4 (n-6) | all-cis-7,10,13,16-docosatetraenoic acid |
| Docosapentaenoic acid | 22:5 (n-6) | all-cis-4,7,10,13,16-docosapentaenoic acid |
| Erucic acid | 22:1 (n-9) | cis-13-docosenoic acid |
| Tetracosapentaenoic acid | 24:5 (n-3) | all-cis-9,12,15,18,21-tetracosapentaenoic acid |
| Tetracosahexaenoic acid | 24:6 (n-3) | all-cis-6,9,12,15,18,21-tetracosahexaenoic acid |
| Tetracosatetraenoic acid | 24:4 (n-6) | all-cis-9,12,15,18-tetracosatetraenoic acid |
| Tetracosapentaenoic acid | 24:5 (n-6) | all-cis-6,9,12,15,18-tetracosapentaenoic acid |
| Nervonic acid | 24:1 (n-9) | cis-15-tetracosenoic acid |

In an embodiment, the polyunsaturated fatty acid produced according to the method has a hydrocarbon backbone composed of 20 to 24 carbon atoms with four or more carbon-carbon double bonds, in particular composed of 20, 22 or 24 carbon atoms with four or more carbon-carbon double bonds. Preferably, the polyunsaturated fatty acid has a hydrocarbon backbone composed of 20 or 22 carbon atoms with four or more carbon-carbon double bonds. More preferably, the polyunsaturated fatty acid produced is arachidonic acid, eicosapentaenoic acid, or docosahexaenoic acid. In a particular embodiment, the polyunsaturated fatty acid produced according to the method of this invention is arachidonic acid.

The microorganism used in the present invention preferably refers to a non-eukaryotic microorganism in particular a bacterium. The bacterium may be, for example but not exclusively, a bacterium belonging to the genus selected from the group consisting of *Bifidobacterium, Lactobacillus* and *Escherichia*. In an embodiment, the bacterium belongs to the genus *Escherichia* and is particularly *Escherichia coli* (*E. coli*). The microorganism is subject to genetic engineering as described further below to produce polyunsaturated fatty acids according to the method.

The term "transgenic" used herein means that the cell of the microorganism, in particular a bacterium, comprises a foreign nucleic acid molecule such as a plasmid which does not exist naturally in the non-genetically modified cells, i.e. wild type of the microorganism. The foreign nucleic acid molecule may be in a form of a recombinant plasmid which comprises different genetic elements in a specific combination or arrangement.

In this invention, the recombinant plasmid is an expression vector carrying an infused polynucleotide and other genetic elements. The polynucleotide in this invention preferably encodes one or more elongase and one or more desaturase. More preferably, the polynucleotide encodes one elongase and at least two desaturases.

The term "elongase" as used refers to a family of enzymes which involves in the elongation of an aliphatic chain of a fatty acid. In particular, the elongase can elongate a polyunsaturated fatty acid at a specific site to insert an ethyl group to the hydrocarbon backbone. The elongase may be, for example but not exclusively, delta 6 elongase, delta 9 elongase or delta 5 elongase.

The term "desaturase" as used refers to a family of enzymes which removes two hydrogen atoms from a hydrocarbon chain of a fatty acid, so as to form an additional carbon-carbon double bond in the hydrocarbon chain. The desaturase may be, for example but not exclusively, delta 6 desaturase, delta 8 desaturase, delta 5 desaturase or delta 4 desaturase.

The elongase in the present invention works jointly with the desaturase to increase the number of carbon atoms of the fatty acid substrate and at the same time introduce at least one carbon-carbon double bond into the fatty acid substrate so as to form the product—polyunsaturated fatty acid whose has a longer hydrocarbon backbone and more carbon-carbon double bonds than the fatty acid substrate. In an embodiment, the polynucleotide in the recombinant plasmid encodes delta 9 elongase, delta 8 desaturase and delta 5 desaturase so as to introduce an ethyl group to the hydrocarbon backbone of the fatty acid substrate and create 2 carbon-carbon double bonds on the hydrocarbon backbone. Preferably, the polynucleotide comprises a first nucleic acid sequence provided in SEQ ID NO: 1 encoding delta 9 elongase, a second nucleic acid sequence provided in SEQ ID NO: 2 encoding delta 8 desaturase and a third nucleic acid sequence provided in SEQ ID NO. 3 encoding delta 5 desaturase. The polyunsaturated fatty acid as obtained in this embodiment thus has a longer hydrocarbon backbone and more carbon-carbon double bonds compared to the fatty acid substrate used. Preferably, the first, second and third nucleic acid sequences are derived from *Euglena Gracilis*.

The "fatty acid substrate" as used in this invention is preferably a polyunsaturated fatty acid having a hydrocarbon backbone composed of 16 to 18 carbon atoms with one or more carbon-carbon double bond. In an embodiment, the fatty acid substrate is a C18 polyunsaturated fatty acid, i.e. composed of 18 carbon atoms, with at least two carbon-carbon double bonds. In a preferred embodiment, the fatty acid substrate is linoleic acid which serves as a carbon source for the production of a polyunsaturated fatty acid having a longer hydrocarbon chain, i.e. composed of more than 18 carbon atoms. Linoleic acid is a relatively cheap feedstock as it is the major constituents of readily available seed oils including soybean oil and sunflower oil. Therefore, it may be more cost worthy to use linoleic acid as a fatty acid substrate.

Referring back to the recombinant plasmid, the recombinant plasmid of the present invention is artificially synthesized by inserting a cassette comprising the polynucleotide as described above to an expression vector. Both the plasmid and the cassette have at least two restriction sites to be cleaved by a restriction enzyme. The cleaved plasmid and cassette are then ligated together by using a ligase and form the recombinant plasmid.

The recombinant plasmid further comprises genetic elements which may involve in the uptake of the fatty acid substrate by the microorganism and the metabolism of the microorganism. In an embodiment, the recombinant plasmid comprises a promoter, a sequence encoding a long-chain fatty acid transport protein precursor, and a sequence encoding a long chain fatty acryl-CoA ligase. The promoter refers to a genetic element on the plasmid that is capable of initiating the transcription of the polynucleotide inserted to the plasmid and other sequences on the plasmid. The long-chain fatty acid transport protein precursor can facilitate the uptake of exogenous carbon source, i.e. the fatty acid substrate in this invention, by the transgenic microorganism by allowing the diffusion of the exogenous carbon source into the periplasm. The long chain fatty acryl-CoA ligase can facilitate the transportation of the carbon source to the cytosol of the microorganism and may involve in the subsequent metabolic pathways.

In addition, the recombinant plasmid further comprises an antibiotic resistance sequence which confers antibiotic resistance to the transgenic microorganism that contain the recombinant plasmid. As such, only those microorganisms harboring a recombinant plasmid can survive in an antibiotic-containing medium and allow to grow and produce the polyunsaturated fatty acid in an medium containing the fatty acid substrate.

Turning to the method of this invention, in step (a), the recombinant plasmid is introduced to the bacterium via a transformation technique such as, but not limited to, heat shock, electroporation, microinjection and particle bombardment. The skilled person is aware of the transformation techniques that are suitable for introducing the recombinant plasmid of the present invention to a microorganism or bacterium. Optionally, after the introduction of the recombinant plasmid, the transgenic bacterium is incubated in an antibiotic-containing medium to screen the transgenic bacterium from the wild type one which does not contain the recombinant plasmid.

The transgenic bacterium containing the recombinant plasmid survives in the antibiotic-containing medium and is separated and collected for incubation in step (b).

In step (b), the transgenic bacterium is incubated in a medium containing the fatty acid substrate as described above under conditions sufficient for the growth of the transgenic bacterium. The medium may be a commercially available prepared medium with an addition of the fatty acid substrate. The person skilled in the art is aware of conditions suitable for growing bacteria.

In step (c), the transgenic bacterium is harvested by performing centrifugation and optionally separation. The collected transgenic bacterium is then subject to extraction to obtain the produced polyunsaturated fatty acids.

In a second aspect, the present invention provides a method of converting linoleic acid to arachidonic acid in particular in a transgenic bacterium, comprising steps of:

(i) preparing a transgenic bacterium by introducing a recombinant plasmid into a bacterium, wherein the recombinant plasmid comprises a polynucleotide encoding one or more elongase and one or more desaturase;
(ii) incubating the transgenic bacterium in a medium containing linoleic acid; and
(iii) harvesting the transgenic bacterium and extracting arachidonic acid from the transgenic bacterium.

The transgenic bacterium is as defined above. In an embodiment, the bacterium belongs to the genus selected from the group consisting of *Bifidobacterium, Lactobacillus* and *Escherichia*. In a particular embodiment herein, the bacterium is *E. Coli*.

The recombinant plasmid is as described above and preferably comprises a polynucleotide encoding one elongase and two desaturases. In an embodiment, the polynucleotide comprises a first nucleic acid sequence provided in SEQ ID NO: 1 encoding delta 9 elongase, a second nucleic acid sequence provided in SEQ ID NO: 2 encoding delta 8 desaturase and a third nucleic acid sequence provided in SEQ ID NO. 3 encoding delta 5 desaturase. The recombinant plasmid further comprises other genetic elements such as, but not limited to, a promoter, a sequence encoding a long-chain fatty acid transport protein precursor, and a sequence encoding a long chain fatty acryl-CoA ligase.

Preferably, the first, second and third nucleic acid sequences are derived from *Euglena Gracilis*.

The inventors found that the application of the transgenic *E. coli* of the present invention allows for a faster and more efficient production of arachidonic acid compared to the existing methods using fungi. The growth rate of the transgenic *E. coli* is approximately 30 min per doubling. In other words, the production time of arachidonic acid can be shortened from 7 days to 2 days, or even shorter based on the exponential nature of microbial growth. The present invention provides an efficient method to produce arachidonic acid, which may also be applied to produce other polyunsaturated fatty acids.

Also, as arachidonic acid may serve as a carbon source for other polyunsaturated fatty acid, the method as disclosed herein is also suitable in the aspect for production of polyunsaturated fatty acid having a longer hydrocarbon backbone than arachidonic acid.

In a third aspect, the present invention provides a cassette comprising a first nucleic acid sequence provided in SEQ ID NO: 1, a second nucleic acid sequence provided in SEQ ID NO: 2 and a third nucleic acid sequence provided in SEQ ID NO. 3 as described above.

Furthermore, the present invention also pertains to a recombinant plasmid comprising a first nucleic acid sequence provided in SEQ ID NO: 1, a second nucleic acid sequence provided in SEQ ID NO: 2, a third nucleic acid sequence provided in SEQ ID NO. 3, a promoter sequence, a sequence encoding a long-chain fatty acid transport protein precursor, and a sequence encoding a long chain fatty acryl-CoA ligase.

EXAMPLES

Example 1

Preparation of the Cassette

Delta 9 elongase, delta 8 desaturase and delta 5 desaturase genes (SEQ ID NO: 1-3) were codon optimized for expression in *E. coli* and were chemically synthesized by Life Technologies as a single continuous cassette. Restriction sites—SpeI and NotI sites were added flanking said cassette during gene synthesis.

Example 2

Preparation of the Recombinant Plasmid

The expression plasmid vector having a sequence as shown in SEQ ID NO: 4 consists of a T7 promoter, fadL and fadD genes. The plasmid vector was linearized by restriction enzymes SpeI and NotI and treated with Shrimp Alkaline Phosphatase. The cassette prepared in Example 1 was also digested by SpeI and NotI. A T4 ligase was used to ligate the resulting linearized plasmid with the digested cassette and a recombinant plasmid was thus obtained.

The recombinant plasmid contains a polycistronic expression system of delta 9 elongase, delta 8 desaturase, delta 5 desaturase, fadL and fadD genes controlled by a single T7 promoter and terminator.

Example 3

Transformation of *E. coli*

The recombinant plasmid were transformed into *E. coli* BL21(de3) using a heat-shock method. Briefly, 50 µL competent cells were thawed on ice for 10 minutes. 50 ng recombinant plasmid DNA was added and the cells were incubated on ice for 30 minutes. The mixture of cells and recombinant plasmid was then subject to heat shock at 42° C. for 10 seconds and was then chilled on ice for 5 minutes. 950 µL of Super Optimal Broth (SOC medium) was added to the mixture and the mixture was incubated at 37° C. with gentle shaking for 1 hour.

Next, 100 µL of the bacterial mixture was spread onto LB plus ampicillin (150 µg/mL) plate and incubated overnight. Successful genetic engineering was confirmed by sequencing of colonies.

Example 4

Production of Polyunsaturated Fatty Acid

The colonies are then selected to grow in a medium containing a fatty acid substrate—linoleic acid under conditions suitable for growth of the *E. coli*. After a period of time, the mixture of medium and transgenic bacteria are collected and separated. The collected bacteria are then subject to homogenization and lysis to release the arachidonic acid produced therein. Subsequent separation, isolation and purification may be performed to obtain the purified arachidonic acid for further applications. For example, the arachidonic acid may be applied in an infant formula to supply nutrients to babies.

For instance, a modified Folch method may be applied to extract the total lipid from the bacterial cells. In particular, the collected bacterial cells are first subject to centrifugation to remove water and supernatants. Second, the obtained cell pellet is treated with 1 ml hexane and 1 ml 14% boron trifluoride in methanol (14% $BF_3$/MeOH) to form a cell suspension. The cell suspension is heated at 100° C. for 1 hour. After the cell lysis, the total lipid are extracted and methylated into fatty acid methyl esters (FAMEs). Then, 1 ml deionized water is added to separate the mixture into two layers. 500 ul of the upper organic layer containing the FAME is collected and dried using a nitrogen steam. Dried samples are re-suspended in 200 ul hexane and transferred to GC-vial for detection.

Example 5

Determination of the Polyunsaturated Fatty Acids Produced

The methylated methyl-arachidonate is identified and quantified by gas chromatography flame ionizing detector (GC-FID) using Agilent 6890 series GC-FID equipped with an autosampler and an Agilent DB-225 capillary column (30 m, 0.35 mm internal diameter, 0.25 um film thickness). Methyl-arachidonate is chosen as the internal standard. The operating conditions are as follows: an autosampler is used to inject the standard and sample. Split-less injection mode is used and the vent is opened after 0.7 min. The injector is held at 220° C./min, and finally the oven temperature is raised to 230° C. at 10 min. The detector is held at 230° C. and helium is used as the carrier gas and the column flow rate is 1 ml/min. 1 ul sample is injected into the GC-FID for each analysis. ARA-FAME is identified according to its specific retention time of the arachidonate standard.

Figure 2:
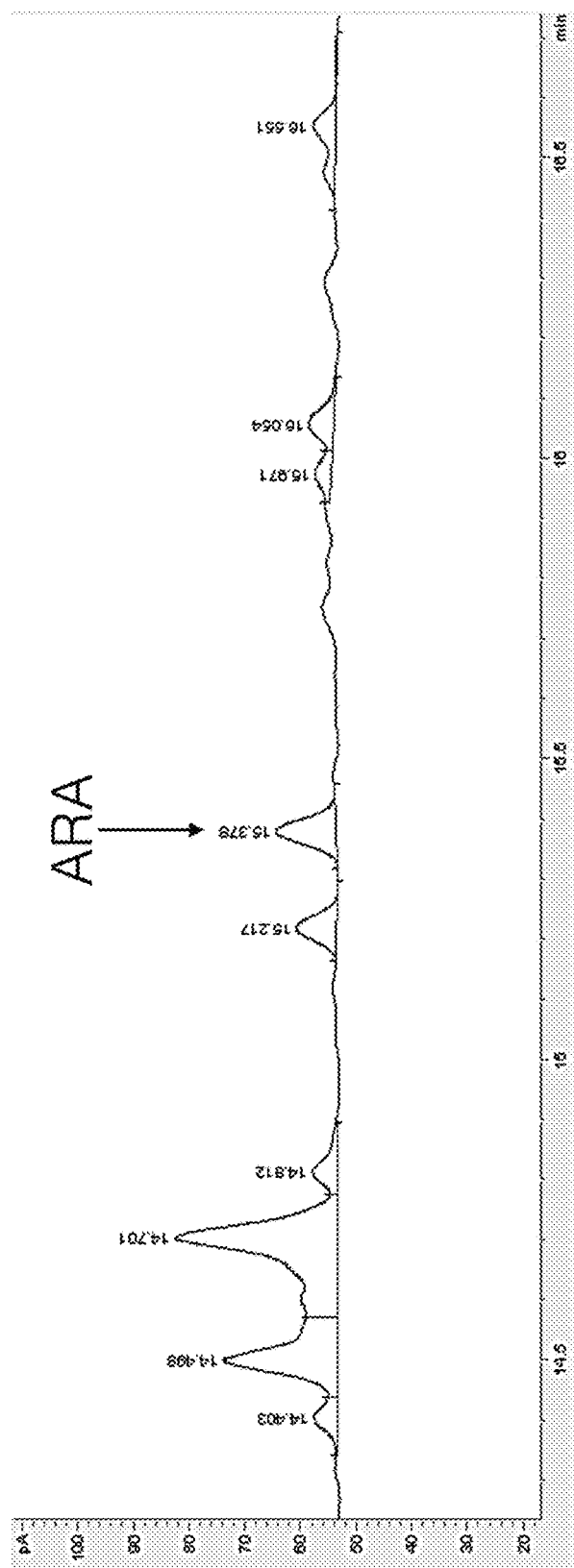
FIG. 2 is a gas chromatogram profile of fatty acids extracted from the transgenic *E. coli* harboring delta 9 elongase, delta 5 desaturase and delta 8 desaturase, and it indicates the corresponding peak of arachidonic acid (ARA).

With reference to FIGS. 1 and 2, it is clear that arachidonic acid was produced by the transgenic *E. coli* while the wild type *E. coli* did not produce arachidonic acid.

Accordingly, it is proved that the method of the present invention is a plausible approach for producing a polyunsaturated fatty acid with the application of a transgenic bacterium.

The invention claimed is:

1. A method of producing a polyunsaturated fatty acid in a transgenic bacterium, wherein the polyunsaturated fatty acid is an omega fatty acid, the method comprising steps of:
   (a) introducing a recombinant plasmid into a bacteria cell to obtain the transgenic bacterium, wherein the recombinant plasmid comprises a polycistronic expression system with a polynucleotide encoding one or more elongase and at least two desaturases, wherein the elongase is selected from delta 6 elongase, delta 9 elongase or delta 5 elongase; and the desaturase is selected from delta 6 desaturase, delta 8 desaturase, delta 5 desaturase or delta 4 desaturase;
   (b) incubating the transgenic bacterium in a medium containing a fatty acid substrate; and
   (c) harvesting the transgenic bacterium and extracting the polyunsaturated fatty acid from the transgenic bacterium.

2. The method of claim 1, wherein the polyunsaturated fatty acid comprises a hydrocarbon backbone composed of 20 to 24 carbon atoms with four or more carbon-carbon double bonds.

3. The method of claim 1, wherein the fatty acid substrate is a polyunsaturated fatty acid and comprises a hydrocarbon backbone composed of 16 to 18 carbon atoms with one or more carbon-carbon double bond.

4. The method of claim 1, wherein the fatty acid substrate is linoleic acid.

5. The method of claim 1, wherein the polynucleotide comprises a first nucleic acid sequence of SEQ ID NO: 1, a second nucleic acid sequence of SEQ ID NO: 2 and a third nucleic acid sequence of SEQ ID NO. 3.

6. The method of claim 1, wherein the recombinant plasmid comprises a promoter, a sequence encoding a long-chain fatty acid transport protein precursor, and a sequence encoding a long chain fatty acryl-CoA ligase.

7. The method of claim 2, wherein the polyunsaturated fatty acid is an omega-3 fatty acid, an omega-6 fatty acid or an omega-9 fatty acid.

8. The method of claim 7, wherein the polyunsaturated fatty acid is arachidonic acid, eicosapentaenoic acid, or docosahexaenoic acid.

9. The method of claim 5, wherein the first, second and third nucleic acid sequences are derived from *Euglena Gracilis*.

10. The method of any one of claim 1, 2, 3, 4, 5, 6, 7, 8, or 9 wherein the bacterium belongs to the genus selected from the group consisting of *Bifidobacterium*, *Lactobacillus* and *Escherichia*.

11. The method of claim 10, wherein the bacterium is *E. coli*.

* * * * *